United States Patent [19]

Aldinger et al.

[11] Patent Number: 5,308,469
[45] Date of Patent: May 3, 1994

[54] OXYGEN SENSOR AND METHOD OF PRODUCING IT

[75] Inventors: Fritz Aldinger, Rodenbach; Harro Bestgen, Kelkheim; Christine Köstler, Bad Soden; Andreas Roosen, Hofheim, all of Fed. Rep. of Germany

[73] Assignee: Hoechst Aktiengesellschaft, Frankfurt am Main, Fed. Rep. of Germany

[21] Appl. No.: 879,795

[22] Filed: May 6, 1992

[30] Foreign Application Priority Data

May 8, 1991 [DE] Fed. Rep. of Germany ....... 4115023

[51] Int. Cl.$^5$ .............................................. G01N 27/26
[52] U.S. Cl. .................................... 204/426; 204/427; 204/435
[58] Field of Search ...................... 204/426, 427, 435

[56] References Cited

U.S. PATENT DOCUMENTS

| | | | |
|---|---|---|---|
| 3,920,172 | 11/1975 | Rhee | 228/121 |
| 4,378,279 | 3/1983 | Habdas et al. | 204/195 S |
| 4,419,213 | 12/1983 | Oshima et al. | 204/426 |
| 4,810,529 | 3/1989 | Mantese et al. | 204/427 |
| 4,839,019 | 6/1989 | Takahama et al. | 204/426 |
| 5,169,512 | 12/1992 | Wiedenmann et al. | 204/426 |

FOREIGN PATENT DOCUMENTS 0148622 7/1985 European Pat. Off. .
0203351 12/1986 European Pat. Off. .
WO89/09933 10/1989 PCT Int'l Appl. .

Primary Examiner—John Niebling
Assistant Examiner—Bruce F. Bell
Attorney, Agent, or Firm—Curtis, Morris & Safford

[57] ABSTRACT

A planar oxygen sensor based on zirconium dioxide is described which is suitable for measuring the oxygen content in combustion furnaces or in the exhaust gases of internal combustion engines. Disposed on an external surface of the sensor is a noble-metal measuring electrode and located in its interior is a reference electrode which is connected to an external contact and is enclosed by two zirconium dioxide layers. One of these layers has, in its region near the edge, a hole whose outwardly pointing part is sealed by a solder glass. The internal part of the hole is partially filled with sintered platinum which makes a conductive connection between a platinum wire, passing outwards through the hole, as external contact and a platinum conductor track which is disposed on the internal interface of the zirconium dioxide layer and which leads to the reference electrode. A method of producing the oxygen sensor is also described.

8 Claims, 2 Drawing Sheets

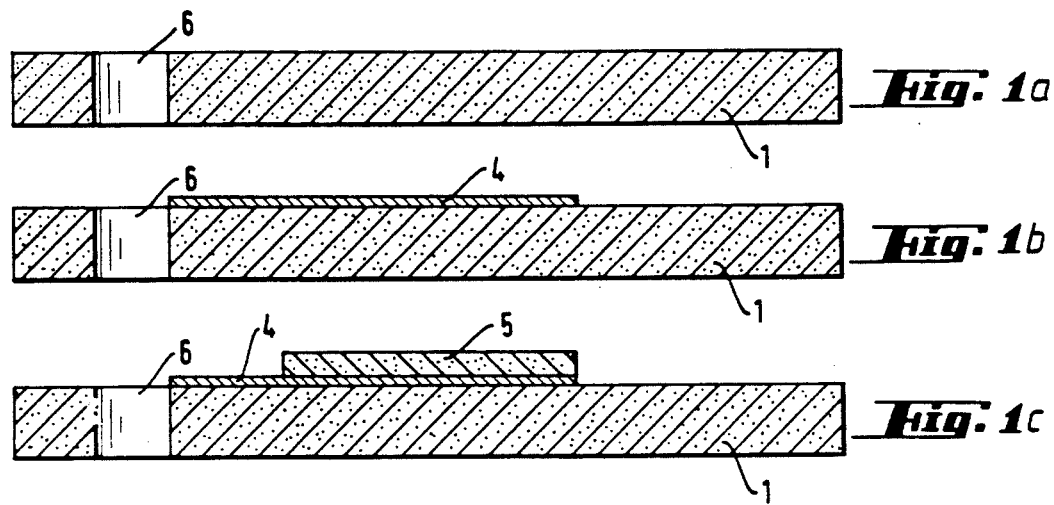
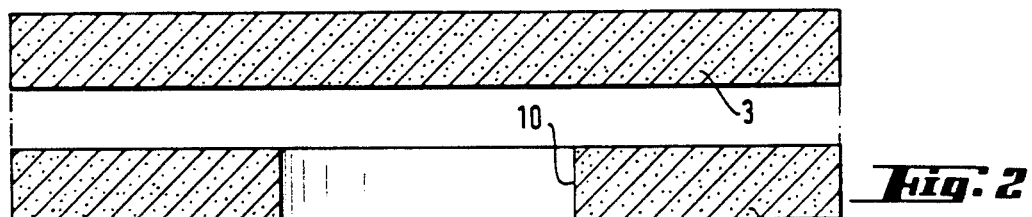

OXYGEN SENSOR AND METHOD OF PRODUCING IT

DESCRIPTION

The present invention relates to a planar oxygen sensor which, when built into a lambda voltage probe, can be used to measure the oxygen content in combustion furnaces or in the exhaust gases of internal combustion engines. The invention further relates to a method of producing such a planar sensor starting from ceramic sheets based on zirconium dioxide.

European Patent 134 709 discloses an elongated oxygen sensor comprising a plurality of stacked flat layers of a solid electrolyte, in particular zirconium dioxide, which sensor has a cavity for a standard substance bounded by at least two of the layers. It furthermore contains a measuring electrode on an external surface and a reference electrode which is in contact with the solid-electrolyte layers and faces the cavity for the standard substance. A solid-electrolyte layer is disposed between measuring electrode and the cavity for the standard substance. Since the cavity for the standard substance in this sensor construction is not fully sealed off from the outside, the supply of a reference gas is necessary for continuous measurements, as intended, under variable conditions. Under these circumstances, a change in the composition of the air or a contamination of the reference system can lead to errors. In addition, the elongated shape of this sensor makes miniaturization difficult.

Investigations have revealed that standard screen printing pastes containing platinum metal yield conductor tracks which are porous and gas-permeable.

The object of the invention was therefore to provide a miniaturized, in particular a planar, gastight sensor construction which makes it possible to use screen printing pastes containing platinum metal to produce the internal reference electrode and the conductor tracks connected thereto and which is universally suitable for the continuous determination of oxygen in combustion exhaust gases of variable composition and temperature.

Surprisingly, an oxygen sensor based on zirconium dioxide has now been found which has an at least three-layer structure composed of two zirconium dioxide external layers and a zirconium dioxide interlayer and has a noble-metal measuring electrode disposed on an external surface of a zirconium dioxide external layer and a reference electrode disposed in the interior and connected to an external contact. This sensor is one wherein the zirconium dioxide external layer which does not carry an external electrode has a hole which is partially filled with a platinum mass which makes the electrical contact between an internal electrode layer and a platinum wire passing outwards through the hole, the remaining space of the hole being filled with a solder glass.

The reference electrode consists of an internal standard in contact with a platinum-metal electrode. The internal standard may be composed, for example, of nickel/nickel oxide or palladium/palladium oxide. The use of the comparison standard palladium/palladium oxide as internal standard is disclosed by German Patent 24 43 037. The use of Ni/NiO to produce a reference oxygen partial pressure is disclosed by German Patent 27 46 381.

A suitable material for the measuring electrode and the platinum layer of the reference electrode is platinum or platinum/rhodium.

The platinum-containing pastes (A and B), with which the platinum wire is fixed in the hole (A) or with which the conductor track leading to the reference electrode in the interior of the sensor is produced (B), are commercially available. The paste for producing the internal standard can be produced from Ni (C) or Pd (D). The pastes may additionally contain organic solvents (for example, terpineol) and organic binders (for example, ethylcellulose). Preferably, the pastes B, C and D are mixed with 5 to 20% by weight of the oxide mixture that is used to construct the zirconium dioxide layers. This addition makes it possible to achieve the result in the case of paste B that the platinum mass adheres well to the zirconium dioxide on sintering and shrinks to the same extent as the zirconium dioxide mass and that the pastes C and D for the internal standard adhere well to the Pt layer and shrink to the same extent as the zirconium dioxide mass.

The zirconium dioxide mass may additionally contain inorganic dopants. Suitable inorganic dopants are CaO, MgO, CeO and $Y_2O_3$. Preferably, the zirconium dioxide mass is doped with $Y_2O_3$. In this way, a large number of vacancies are produced for $O^{2-}$ ions and these bring about the ionic conductivity of the ceramic. In the range between 3.5 and 14.0% by weight of $Y_2O_3$, preferably from 5 to 10% by weight, based on the total quantity of zirconium dioxide mass, the ion conductivity is adequate for the sensor to be used in lambda probes. The Y content furthermore improves the thermal shock stability of the sensor. Oxide mixtures containing 5% by weight of $Y_2O_3$ result in purely tetragonal grains. Ratios containing 10% by weight of $Y_2O_3$ result in a mixture of tetragonal and cubic grains. In both cases, undesirable crack spreading in the ceramic is impeded or completely suppressed by a so-called internal work hardening. The use of a zirconium dioxide containing $Y_2O_3$ is disclosed, inter alia, by German Patent 35 37 709, German Patent 35 43 818 and German Offenlegungsschrift 34 26 597.

The solder glass used to seal the platinum-wire feed through should if possible have a coefficient of thermal expansion which matches that of $ZrO_2$ ($1 \times 10^{-5}$/K). Glasses composed of Cao, $Al_2O_3$, $SiO_2$ and, possibly, PbO can be used for this purpose. At the operating temperatures of the sensor, the solder glass may at most exhibit an insignificant conductivity due to transport of $O^{2-}$. $ZrO_2$ contents in the glass are therefore harmful. The softening point of the solder glass should be 800°–1400° C. so that the serviceability desired by the automobile industry can be complied with. The softening point of the solder glass is preferably about 50° C.–100° C. higher than maximum the application temperature of the sensor. For an application temperature of up to 1000° C., a solder glass has therefore to be used which sinters at 1050°–1100° C. The softening point of the solder glass is below the melting point of the platinum metal of the pastes. Suitable glasses for the solder glass used within the scope of the invention are described in the publication entitled "Glas, Glaskeramik und Sinterglaskeramik" ("Glass, glass ceramic and sintered-glass ceramic"), Chemie-Ingenieur-Technik 37 (1965), 1145. A particularly preferred glass has the following composition: 45.8% by weight of $SiO_2$, 32.4% by weight of MgO and 21.8% by weight of $Al_2O_3$.

An electrical heating element is preferably disposed on the outer side of the planar sensor according to the invention which is opposite the external measuring electrode. A heating element enables a reliable oxygen determination in combustion exhaust gases even if these are still cold or have not yet reached a certain temperature. The heating element preferably has a laminar structure. In this connection, a meander-type heating conductor which is composed of a suitable refractory metal of low conductivity (for example, tungsten) and which can be connected to a current source by two outwardly pointing contact pins is present in the interior of an electrically insulating ceramic such as, for example, $Al_2O_3$. Said heating element may be joined mechanically (for example, by a pressure-contact spring) to the sensor according to the invention. If the platinum wire connected to the reference electrode is disposed on the same side of the sensor, it may be necessary for the heating element to have a cutout through which the platinum wire is fed.

For the purpose of use, the sensor is normally installed in a tubular lambda probe in such a way that the planes of the layers are perpendicular to the tube axis. The geometrical dimensions of the planar sensor are chosen as desired. It may be, for example, rectangular or square. Expedient for the installation and therefore preferred is a roughly circular shape. The thickness of the sensor (without heating element) is preferably about 1 to 2 mm. The outside diameter is preferably 5–10 mm.

In a further development of the sensor according to the invention, the zirconium dioxide central layer also additionally has a hole which is disposed at the position of the hole in the zirconium dioxide external layer and which is also partially filled with a platinum mass and with a solder glass. This development makes it possible to vary the geometrical arrangement of the reference electrode in the interior of the sensor for production-engineering reasons.

The invention furthermore relates to a method of producing a planar zirconium dioxide sensor which is suitable for measuring the oxygen content in the exhaust gases of internal combustion engines or combustion furnaces and which has a reference electrode with an electrical conductor track leading outwards in the interior and a noble-metal measuring electrode on an external surface. The method comprises casting a liquid ceramic sheet casting mass containing organic additives, in particular a volatile organic solvent, finely divided zirconium dioxide and inorganic dopants onto a flat substrate and, in doing so, producing a thin film, drying the film and peeling it off the substrate, punching out of the dried film a plurality of equally large cards which correspond roughly to the dimensions of the future probe, punching a hole near the edge in at least a first card and applying to one surface of a first card a conductor track extending from the hole to the central region of the card by printing on a platinum-metal paste (B), printing on a paste (C or D) over the conductor track in the central region of the card, which paste later forms an internal standard, applying at least one second card having a hole in the central region to said first surface in such a way that the paste (C or D) for the internal standard is enclosed by it, applying at least one unperforated third card to said second card in such a way that the central region partially filled with paste (C or D) is covered, introducing some platinum-metal paste (A) into the hole near the edge of the first card in the vicinity of the adjacent second card and then introducing into said paste a platinum-metal wire whose cross section fills about 10 to 80% of the area of the hole near the edge, firing said card structure oxidatively at 1400° to 1600° C., in which process the cards sinter together to form a zirconium dioxide sensor, completely filling the space of the hole near the edge not filled with platinum-metal wire with a powdered solder glass and firing the sensor a second time at 800° to 1400° C., in which process the solder glass sinters together to form a glass which fills the hole near the edge in a gastight manner, printing the unperforated surface of the sensor by the screen-printing method with a conductive platinum-metal paste (B) at least partially up to the edge and firing the sensor a third time oxidatively at 800° to 1000° C., in which process the measuring electrode is formed from the paste (B).

In order to reduce the number of firings, the platinum-containing paste (B) for producing the external measuring electrode can also already be applied to the unperforated surface of the sensor in the green state. Instead of applying a paste, the platinum may also be sputtered on or deposited by chemical vapor deposition at this point. The first, second and third card may also be punched out in such a large form that between 30 and 50 sensors, in particular 40 sensors can be produced simultaneously as a multiple printed panel and punched out before the first sinter firing.

The liquid ceramic sheet casting mass used contains, as organic additive, in particular binder, dispersant, a volatile solvent (for example trichloroethylene/alcohol) and plasticizer. The substrate used for casting may be a steel plate, a moving steel strip or a smooth plastic sheet, for example a polyester sheet. The thickness of the film produced is about 0.2 to 2 mm, preferably 0.40–0.8 mm. A constant layer thickness of the thin film can be obtained by using a casting shoe. The drying of the film may also be carried out continuously. The dimensions of the punched cards shrink during the ceramic firing as a function of the proportion by volume of organic components by 10 to 30%, in particular 22 to 25%.

In total, at least three cards are needed to produce the sensor. Advantageously, at least two first cards, at least one second card and at least two third cards are used.

The measuring electrode is preferably partially coated with a thin, porous, nonconducting protective layer of ceramic material to protect it against impurities. For example, a mixture of $Al_2O_3$ and MgO which produces mullite or a spinel can be applied to the measuring electrode in a thin layer with the aid of a thermal spraying method.

The diameter of the hole near the edge is about 0.8 to 2 mm, in particular 1.2 to 1.5 mm. The distance from the edge is at least 1 mm, preferably at least 1.5 mm. The total area of the hole in the central region of the $ZrO_2$ interlayer used to produce the reference electrode should be at least 1 mm². Larger cross sections result in a better functioning of the internal standard. Preferably, the hole disposed in the central region is circular. The geometrical shape and size of the hole may correspond to the area which is printed with the paste (C) or (D) on the first surface of the first card.

The metal paste for producing the internal standard may contain palladium (C) as essential constituent. After an oxidative firing, this paste is present as a metal/metal oxide mixture Pd/PdO. However, a paste based on nickel powder (D) and organic additives (solvent, binder) may also be used. The mixture of Ni/NiO resulting therefrom in the oxidative firing can also be used as an internal standard. In both cases, an atmosphere having a defined oxygen partial pressure and a defined temperature dependence forms over the metal/metal oxide mixture.

BRIEF DESCRIPTION OF THE DRAWINGS

FIGS. 1(a-c) show the production of a green sheet card with internal standard coated with platinum paste.

FIG. 2 shows in an exploded drawing how the arrangement according to FIG. 1c is completed to form a green sensor.

FIG. 3 shows a perpendicular section through a finished sensor in side view of the external contact to the conductor track in the interior of the sensor after firing.

DETAILED DESCRIPTION OF THE DRAWINGS

Figure 4:
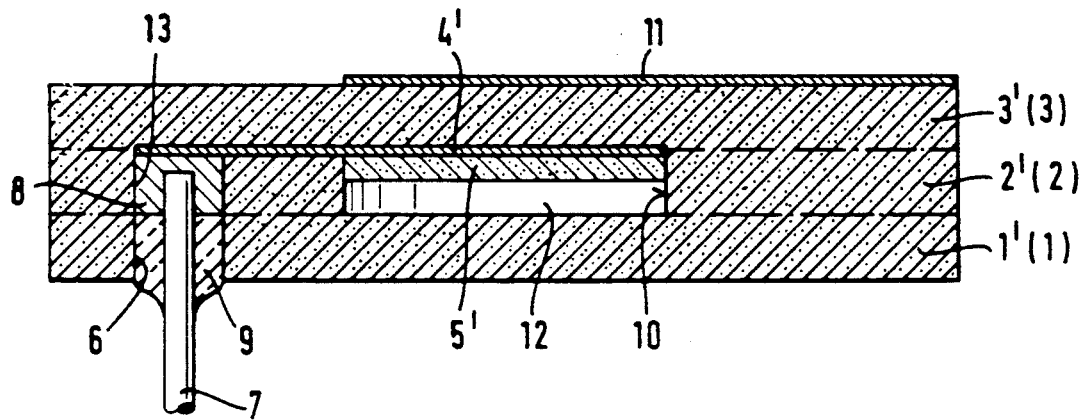
FIGS. 4 and 5 show a vertical section of a sensor in side view.

The invention is explained in greater detail by way of example by reference to the figures. FIG. 1 (a, b, c) shows the production of a green sheet card with internal standard coated with platinum paste. A track 4 of a platinum-containing paste and a layer 5 on top thereof from which the internal standard (for example Ni/NiO) is produced by heating are first deposited by screen printing on a sheet card 1 having a hole 6 in the region near the edge. The track 4 extends from the hole 6 near the edge to the central region of the sheet card 1. The layer 5 may be produced, for example, by screen printing. Preferably, the layer 5 applied in the central region of the card 1 has the shape of a round tablet and, preferably, the track situated underneath has the same shape and size.

FIG. 2 shows in an exploded drawing how the arrangement according to FIG. 1c is completed to form a green sensor. For this purpose, a sheet card 2 having a hole 10 in the central region is first laid on the arrangement according to FIG. 1c. Then a further sheet card 3 without hole, which may optionally already have the external measuring electrode, is then laid on and the arrangement so produced is laminated together. It is advantageous to coat the region of the sheet card 2 situated opposite the hole 6 with a platinum-containing paste as well in order to improve the electrical connection of the external contact to the internal reference electrode comprising track 4 and layer 5.

FIG. 3 shows a perpendicular section through a finished sensor in side view, in particular the connection of the external contact to the conductor track in the interior of the sensor after firing.

The platinum wire 7 terminates in the platinum mass 8 which has been produced after firing from the platinum-containing paste (A) introduced into the hole 6. The remainder of the hole 6 is filled with the solder glass 9 which is produced by pouring-in a solder-glass powder or a solder-glass paste or laying-on a prestressed solder-glass ring along with subsequent sintering. The conductor track 4', produced by firing-in a platinum-containing paste, may also cover the cross section of the hole 6, but this is not shown in FIG. 3. The layer 5 has been converted into the internal standard 5' during firing. The external measuring electrode 11 is deposited in a manner known per se. Preferably, it extends over the reference electrode. The individual layers 1, 2 and 3 are converted during firing into a cohesive sintered body in which the individual fired layers 1', 2' and 3' can be distinguished only by sectioning and observing under the microscope. The space 12 above the internal standard 5' is filled with gas and has a defined, temperature-dependent oxygen partial pressure.

FIG. 4 shows a vertical section through another embodiment of a sensor in side view.

In the embodiment shown in FIG. 4, the card 1 has only a hole 6 provided at the side, while the card 2 has, in addition to the hole 10 in the central region, also an additional hole 13 provided at the side and the card 3 carries on the side opposite the external measuring electrode 11, the platinum track 4' deposited by screen printing and, on top thereof, the layer 5' for producing the internal standard. The laminating, sintering, contacting of the reference electrode with a platinum wire 7 and the introduction of the solder glass 9 can be carried out as described and result in the sensor shown.

Figure 5:
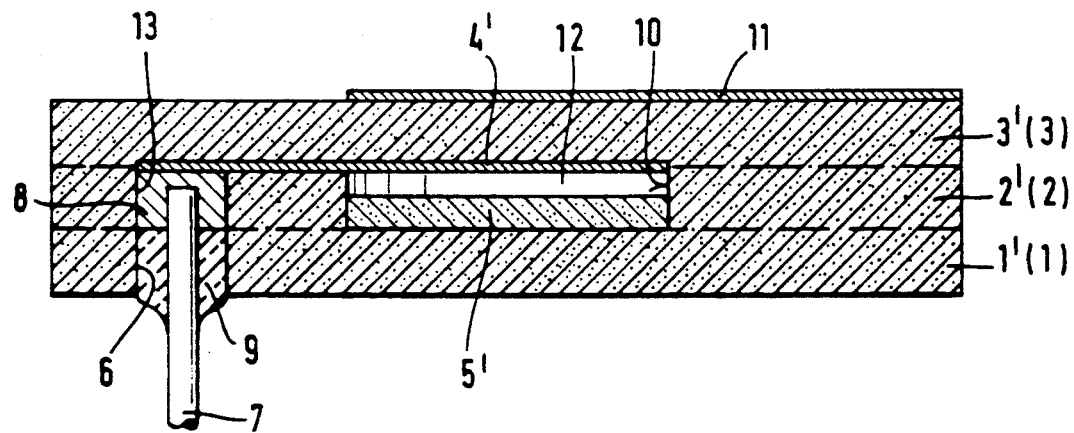

FIG. 5 shows a vertical section through a further embodiment of a sensor according to the invention in side view. Identical reference numerals in this representation have the same meaning as in the preceding figures. The difference in the embodiment shown in FIG. 5 compared with the embodiment shown in FIG. 4 is that the layer 5', which forms the internal standard, is in direct contact with the sheet card 1, whereas the track 4' is in direct contact with the sheet card 3 carrying the measuring electrode 11.

We claim:

1. A planar oxygen sensor based on zirconium dioxide for measuring the oxygen content in combustion furnaces or in the exhaust gases of internal combustion engines, which has an at least three-layer structure composed of two zirconium dioxide external layers and a zirconium dioxide central layer and has a noble-metal measuring electrode disposed on an external surface of a zirconium dioxide external layer and a reference electrode disposed entirely in the interior of said zirconium dioxide central layer and conductably connected to an external contact, wherein the zirconium dioxide external layer which does not carry an external electrode has an opening which is partially filled with a platinum mass which permits electrical connection between said reference electrode and said external contact formed of a platinum wire extending throughout said opening and outwardly of said external electrode, the remaining space of said opening being filled with a solder glass.

2. An oxygen sensor as claimed in claim 1, wherein the zirconium dioxide layers additionally contains 3.5 to 14.0% by weight of $Y_2O_3$.

3. An oxygen sensor as claimed in claim 1, wherein an electrical heating element is disposed on the outside side opposite the external measuring electrode.

4. An oxygen sensor as claimed in claim 1, which has a roughly circular geometrical dimension having an outside diameter of 5 to 10 mm and a thickness in the range from 1 to 2 mm.

5. An oxygen sensor as claimed in claim 1, wherein the zirconium dioxide central layer additionally also has an opening which is disposed at the position of the opening in the zirconium dioxide external layer and which is also partially filled with a platinum mass and with a solder glass.

6. An oxygen sensor as claimed in claim 1, wherein the zirconium dioxide layers additionally contains 5 to 10% by weight of $Y_2O_3$.

7. A planar oxygen sensor based on zirconium dioxide for measuring the oxygen content in combustion furnaces or in the exhaust gases of internal combustion engines, which has an at least three-layer structure composed of two zirconium dioxide external layers and a zirconium dioxide central layer and has a noble-metal measuring electrode disposed on an external surface of a zirconium dioxide external layer and a reference electrode disposed entirely in the interior of said zirconium dioxide central layer and conductably connected to an external contact disposed generally perpendicular to said reference electrode, wherein the zirconium dioxide external layer which does not carry an external electrode has an opening which is partially filled with a platinum mass which permits electrical connection between said reference electrode and said external contact formed of a platinum wire extending throughout said opening and outwardly of said external electrode, the remaining space of said opening being filled with a solder glass.

8. A planar oxygen sensor based on zirconium dioxide for measuring the oxygen content in combustion furnaces or in the exhaust gases of internal combustion engines, which has an at least three-layer structure composed of two zirconium dioxide external layers and a zirconium dioxide central layer and has a noble-metal measuring electrode disposed on an external surface of a zirconium dioxide external layer and a reference electrode disposed entirely in the interior of said zirconium dioxide central layer in an inner cavity of said zirconium dioxide central layer, said reference electrode being conductably connected to an external contact disposed generally perpendicular to said reference electrode, wherein the zirconium dioxide external layer which does not carry an external electrode has an opening which is partially filled with a platinum mass which permits electrical connection between said reference electrode and said external contact formed of a platinum wiring extending throughout said opening and outwardly of said external electrode, the remaining space of said opening being filled with a solder glass.

* * * * *